(12) United States Patent
Johnson

(10) Patent No.: US 10,420,583 B2
(45) Date of Patent: Sep. 24, 2019

(54) METHODS AND APPARATUS FOR CONTROLLING SURGICAL INSTRUMENTS USING A PORT ASSEMBLY

(71) Applicant: Covidien LP, Mansfield, MA (US)

(72) Inventor: Kristin D. Johnson, Louisville, CO (US)

(73) Assignee: Covidien LP, Mansfield, MA (US)

( * ) Notice: Subject to any disclaimer, the term of this patent is extended or adjusted under 35 U.S.C. 154(b) by 614 days.

(21) Appl. No.: 14/786,280

(22) PCT Filed: May 22, 2014

(86) PCT No.: PCT/US2014/039203
§ 371 (c)(1),
(2) Date: Oct. 22, 2015

(87) PCT Pub. No.: WO2014/190185
PCT Pub. Date: Nov. 27, 2014

(65) Prior Publication Data
US 2016/0089181 A1    Mar. 31, 2016

Related U.S. Application Data

(60) Provisional application No. 61/826,395, filed on May 22, 2013.

(51) Int. Cl.
*A61B 17/34* (2006.01)
*A61M 39/02* (2006.01)
(Continued)

(52) U.S. Cl.
CPC ...... *A61B 17/3423* (2013.01); *A61B 1/00087* (2013.01); *A61B 1/05* (2013.01);
(Continued)

(58) Field of Classification Search
CPC ............ A61B 17/3403; A61B 17/3421; A61B 2017/3409; A61B 17/3423; A61M 39/0247; A61M 2039/0279; A61M 2039/0267
See application file for complete search history.

(56) References Cited

U.S. PATENT DOCUMENTS 3,402,710 A    9/1968  Paleschuck
3,777,757 A   12/1973  Gray et al.
(Continued)

FOREIGN PATENT DOCUMENTS

CA    2702419 A1   11/2010
EP    1312318 A1    5/2003
(Continued)

OTHER PUBLICATIONS

Milton et al. 2005 Optical Engineering 44:123402 8 pages.*
(Continued)

*Primary Examiner* — Baisakhi Roy
*Assistant Examiner* — Patrick M Mehl

(57) ABSTRACT

A surgical port assembly for use with surgical instruments includes a body including an exterior surface and an interior space defined by an interior surface of the body. The surgical port assembly includes a control interface including a plurality of drive members coupled to the body and controllable to apply a force to a different portion of a shaft of an surgical instrument, when the shaft is disposed within the interior space, to move a distal portion of the surgical instrument to a desired position within a body cavity.

14 Claims, 8 Drawing Sheets

(51) Int. Cl.
*A61B 1/00* (2006.01)
*A61B 1/05* (2006.01)
*A61B 1/313* (2006.01)
*A61B 17/02* (2006.01)
*A61B 17/00* (2006.01)
*A61B 19/00* (2006.01)

(52) U.S. Cl.
CPC ........ *A61B 1/3132* (2013.01); *A61B 17/0218* (2013.01); *A61B 17/3403* (2013.01); *A61B 17/3421* (2013.01); *A61M 39/0247* (2013.01); *A61B 2017/00022* (2013.01); *A61B 2017/00535* (2013.01); *A61B 2017/347* (2013.01); *A61B 2017/3409* (2013.01); *A61B 2019/5272* (2013.01); *A61M 2039/0267* (2013.01); *A61M 2039/0279* (2013.01)

(56) References Cited

U.S. PATENT DOCUMENTS

| | | | |
|---|---|---|---|
| 4,112,932 A | 9/1978 | Chiulli | |
| 5,209,741 A | 5/1993 | Spaeth | |
| 5,269,772 A | 12/1993 | Wilk | |
| 5,312,417 A | 5/1994 | Wilk | |
| 5,342,385 A | 8/1994 | Norelli et al. | |
| 5,391,156 A | 2/1995 | Hildwein et al. | |
| 5,395,367 A | 3/1995 | Wilk | |
| 5,454,367 A | 10/1995 | Moll et al. | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,524,644 A | 6/1996 | Crook | |
| 5,545,150 A | 8/1996 | Danks et al. | |
| 5,572,999 A | 11/1996 | Funda et al. | |
| 5,634,911 A | 6/1997 | Hermann et al. | |
| 5,634,937 A | 6/1997 | Mollenauer et al. | |
| 5,766,126 A | 6/1998 | Anderson | |
| 5,797,835 A | 8/1998 | Green | |
| 5,803,921 A | 9/1998 | Bonadio | |
| 5,830,191 A | 11/1998 | Hildwein et al. | |
| 5,833,603 A | 11/1998 | Kovacs et al. | |
| 5,904,703 A | 5/1999 | Gilson | |
| 5,906,577 A | 5/1999 | Beane et al. | |
| 5,911,757 A | 6/1999 | Seare, Jr. | |
| 6,004,303 A | 12/1999 | Peterson | |
| 6,033,426 A * | 3/2000 | Kaji ........ | A61B 42/10 600/207 |
| 6,048,309 A | 4/2000 | Flom et al. | |
| 6,080,181 A | 6/2000 | Jensen et al. | |
| 6,440,063 B1 | 8/2002 | Beane et al. | |
| 6,486,588 B2 | 11/2002 | Doran et al. | |
| 6,551,270 B1 | 4/2003 | Bimbo et al. | |
| 6,562,022 B2 | 5/2003 | Hoste et al. | |
| 6,578,577 B2 | 6/2003 | Bonadio et al. | |
| 6,645,196 B1 | 11/2003 | Nixon et al. | |
| 6,723,088 B2 | 4/2004 | Gaskill, III et al. | |
| 6,770,081 B1 | 8/2004 | Cooper et al. | |
| 6,834,243 B2 * | 12/2004 | Zemer ........ | G01R 31/2887 324/750.22 |
| 6,929,637 B2 | 8/2005 | Gonzalez et al. | |
| 7,008,377 B2 | 3/2006 | Beane et al. | |
| 7,011,645 B2 | 3/2006 | McGuckin, Jr. et al. | |
| 7,052,454 B2 | 5/2006 | Taylor | |
| 7,125,382 B2 | 10/2006 | Zhou et al. | |
| 7,297,112 B2 | 11/2007 | Zhou et al. | |
| 7,300,399 B2 | 11/2007 | Bonadio et al. | |
| 7,347,862 B2 | 3/2008 | Layer | |
| 7,416,530 B2 | 8/2008 | Turner et al. | |
| 7,473,221 B2 | 1/2009 | Ewers et al. | |
| 7,559,893 B2 | 7/2009 | Bonadio et al. | |
| 7,563,250 B2 | 7/2009 | Wenchell | |
| 7,657,297 B2 | 2/2010 | Simpson et al. | |
| 7,686,762 B1 | 3/2010 | Najafi et al. | |
| 7,758,500 B2 | 7/2010 | Boyd et al. | |
| 7,766,824 B2 | 8/2010 | Jensen et al. | |
| 7,787,963 B2 | 8/2010 | Geistert et al. | |
| 7,798,998 B2 | 9/2010 | Thompson et al. | |
| 7,841,980 B2 * | 11/2010 | Minosawa ........ | A61B 1/00177 600/103 |
| 7,850,600 B1 | 12/2010 | Piskun | |
| 7,998,118 B2 | 8/2011 | Rockrohr | |
| 8,033,995 B2 | 10/2011 | Cropper et al. | |
| 8,157,786 B2 | 4/2012 | Miller et al. | |
| 8,187,177 B2 | 5/2012 | Kahle et al. | |
| 8,187,178 B2 | 5/2012 | Bonadio et al. | |
| 8,257,253 B2 | 9/2012 | Piskun | |
| 8,641,610 B2 | 2/2014 | Okoniewski et al. | |
| 2001/0038258 A1 * | 11/2001 | Fischer ........ | H02N 2/0095 310/328 |
| 2002/0019635 A1 | 2/2002 | Wenstrom et al. | |
| 2003/0014076 A1 | 1/2003 | Mollenauer et al. | |
| 2003/0093104 A1 | 5/2003 | Bonner et al. | |
| 2003/0130648 A1 | 7/2003 | Jensen et al. | |
| 2003/0208207 A1 * | 11/2003 | Layer ........ | A61B 19/00 606/130 |
| 2004/0092795 A1 | 5/2004 | Bonadio et al. | |
| 2004/0236192 A1 | 11/2004 | Necola Shehada et al. | |
| 2005/0004478 A1 | 1/2005 | Fitz | |
| 2005/0096695 A1 | 5/2005 | Olich | |
| 2005/0165317 A1 | 7/2005 | Turner et al. | |
| 2005/0283140 A1 | 12/2005 | Jensen et al. | |
| 2006/0020241 A1 | 1/2006 | Piskun et al. | |
| 2006/0149306 A1 | 7/2006 | Hart et al. | |
| 2006/0161049 A1 | 7/2006 | Beane et al. | |
| 2006/0167440 A1 | 7/2006 | Cooper et al. | |
| 2006/0200012 A1 | 9/2006 | Mansour et al. | |
| 2006/0200220 A1 | 9/2006 | Brown et al. | |
| 2006/0247500 A1 | 11/2006 | Voegele et al. | |
| 2006/0247516 A1 | 11/2006 | Hess et al. | |
| 2006/0247673 A1 | 11/2006 | Voegele et al. | |
| 2006/0247678 A1 | 11/2006 | Weisenburgh et al. | |
| 2006/0270911 A1 | 11/2006 | Voegele et al. | |
| 2007/0005045 A1 | 1/2007 | Mintz et al. | |
| 2007/0027371 A1 | 2/2007 | Benaron et al. | |
| 2007/0060884 A1 | 3/2007 | Hayek | |
| 2007/0119274 A1 | 5/2007 | Devengenzo et al. | |
| 2007/0137371 A1 | 6/2007 | Devengenzo et al. | |
| 2007/0142823 A1 | 6/2007 | Prisco et al. | |
| 2007/0265502 A1 | 11/2007 | Minosawa et al. | |
| 2008/0027476 A1 | 1/2008 | Piskun | |
| 2008/0033273 A1 | 2/2008 | Zhou et al. | |
| 2008/0033453 A1 | 2/2008 | Brock | |
| 2008/0058652 A1 | 3/2008 | Payne | |
| 2008/0058728 A1 | 3/2008 | Soltz et al. | |
| 2008/0097332 A1 | 4/2008 | Greenhalgh et al. | |
| 2008/0108885 A1 | 5/2008 | Colvin | |
| 2008/0154101 A1 | 6/2008 | Jain et al. | |
| 2008/0161826 A1 | 7/2008 | Guiraudon | |
| 2008/0188868 A1 | 8/2008 | Weitzner et al. | |
| 2008/0255519 A1 | 10/2008 | Piskun et al. | |
| 2008/0287788 A1 | 11/2008 | Richardson et al. | |
| 2009/0024142 A1 | 1/2009 | Ruiz Morales | |
| 2009/0054908 A1 | 2/2009 | Zand et al. | |
| 2009/0062604 A1 | 3/2009 | Minosawa | |
| 2009/0088775 A1 | 4/2009 | Swarup et al. | |
| 2009/0093752 A1 | 4/2009 | Richard et al. | |
| 2009/0093850 A1 | 4/2009 | Richard | |
| 2009/0163782 A1 | 6/2009 | Shehada et al. | |
| 2009/0209969 A1 | 8/2009 | Wolfe | |
| 2009/0248038 A1 | 10/2009 | Blumenkranz et al. | |
| 2009/0299153 A1 | 12/2009 | Gerber et al. | |
| 2009/0326324 A1 | 12/2009 | Munoz Martinez et al. | |
| 2010/0016800 A1 | 1/2010 | Rockrohr | |
| 2010/0022825 A1 * | 1/2010 | Yoshie ........ | A61B 1/00133 600/104 |
| 2010/0063452 A1 | 3/2010 | Edelman et al. | |
| 2010/0076259 A1 * | 3/2010 | Asada ........ | A61B 1/00096 600/102 |
| 2010/0081880 A1 | 4/2010 | Widenhouse et al. | |
| 2010/0081895 A1 | 4/2010 | Zand | |
| 2010/0100043 A1 | 4/2010 | Racenet | |

(56) References Cited

U.S. PATENT DOCUMENTS

| | | |
|---|---|---|
| 2010/0198215 A1 | 8/2010 | Julian et al. |
| 2010/0204713 A1 | 8/2010 | Ruiz Morales |
| 2010/0228092 A1* | 9/2010 | Ortiz ............... A61B 17/3423 600/204 |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0280326 A1 | 11/2010 | Hess et al. |
| 2010/0286484 A1 | 11/2010 | Stellon et al. |
| 2010/0298646 A1 | 11/2010 | Stellon et al. |
| 2010/0312060 A1 | 12/2010 | Widenhouse et al. |
| 2010/0312065 A1 | 12/2010 | Shelton, IV et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0071347 A1 | 3/2011 | Rogers et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0098531 A1* | 4/2011 | To ................... A61B 17/0218 600/114 |
| 2011/0125186 A1 | 5/2011 | Fowler et al. |
| 2011/0166423 A1 | 7/2011 | Farascioni et al. |
| 2011/0190590 A1 | 8/2011 | Wingardner, III et al. |
| 2011/0208007 A1 | 8/2011 | Shohat et al. |
| 2011/0218551 A1 | 9/2011 | Devengenzo et al. |
| 2011/0245844 A1 | 10/2011 | Jinno |
| 2011/0295315 A1 | 12/2011 | Jensen et al. |
| 2012/0022334 A1 | 1/2012 | Piskun |
| 2012/0209291 A1 | 8/2012 | Anderson et al. |
| 2012/0253132 A1 | 10/2012 | Davis |
| 2012/0259345 A1 | 10/2012 | Julian et al. |
| 2012/0259582 A1 | 10/2012 | Gloger |
| 2013/0035697 A1 | 2/2013 | Ogawa et al. |
| 2013/0144116 A1 | 6/2013 | Cooper et al. |
| 2013/0204271 A1 | 8/2013 | Brisson et al. |
| 2013/0331858 A1 | 12/2013 | Devengenzo et al. |

FOREIGN PATENT DOCUMENTS

| | | |
|---|---|---|
| EP | 2044889 A1 | 4/2009 |
| EP | 2095781 A2 | 9/2009 |
| EP | 2098182 A2 | 9/2009 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2248478 A1 | 11/2010 |
| EP | 2253283 A1 | 11/2010 |
| EP | 2272450 A2 | 1/2011 |
| EP | 2292165 | 3/2011 |
| EP | 2471484 A2 | 7/2012 |
| EP | 2979608 A1 | 2/2016 |
| WO | 93/14801 | 8/1993 |
| WO | 2004/054456 | 7/2004 |
| WO | 2008/121294 A1 | 10/2008 |
| WO | 2009/036343 | 3/2009 |
| WO | 2010/141409 | 12/2010 |
| WO | 2011/153083 A2 | 12/2011 |

OTHER PUBLICATIONS

International Search Report for (PCT/US2014/039203) date of completion is Sep. 12, 2014 (5 pages).
European Search Report 11194126.6-2310 dated Feb. 5, 2012.
European Search Report 11250792.6-310 dated Feb. 24, 2012.
Extended European Search Report corresponding to counterpart Int'l Appln. No. EP 14 80 0244.7 dated Jan. 3, 2017.
Chinese First Office Action corresponding to counterpart Int'l Appln. No. CN 2014800294906 dated Jun. 27, 2017.
Chinese Second Office Action corresponding to counterpart Patent Appln. No. CN 2014800294906 dated Mar. 2, 2018.

* cited by examiner

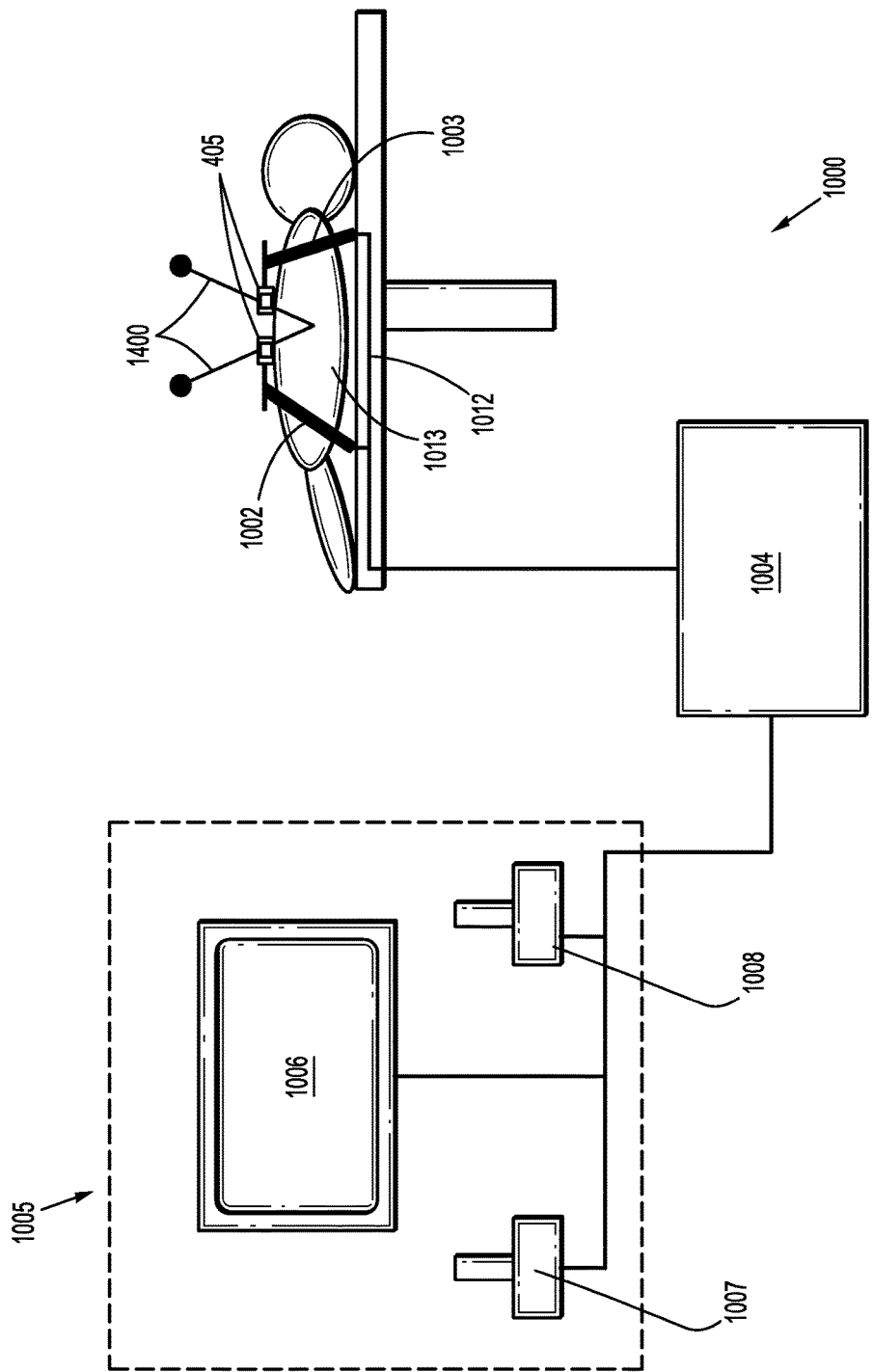

METHODS AND APPARATUS FOR CONTROLLING SURGICAL INSTRUMENTS USING A PORT ASSEMBLY

CROSS-REFERENCE TO RELATED APPLICATIONS

This application is a U.S. National Stage application filed under 35 U.S.C. § 371(a) of International Patent Application No. PCT/US2014/039203, filed May 22, 2014, which claims benefit of, and priority to, U.S. Provisional Patent Application Ser. No. 61/826,395, filed on May 22, 2013, the entire content of which is incorporated herein by reference.

BACKGROUND

1. Technical Field

The present disclosure relates to minimally-invasive surgery. More particularly, the present disclosure relates to methods and apparatus for controlling surgical instruments using a port assembly.

2. Background of Related Art

Surgical techniques and instruments have been developed that allow the surgeon to perform an increasing range of surgical procedures with minimal incisions into the skin and body tissue of the patient. Minimally-invasive surgery has become widely accepted in many medical specialties, often replacing traditional open surgery. Unlike open surgery, which requires a long incision, minimally-invasive procedures, such as endoscopy or laparoscopy, are performed through one or more short incisions, with much less trauma to the body.

In laparoscopic and endoscopic surgical procedures, a small "keyhole" incision or puncture is made in a patient's body, e.g., in the abdomen, to provide an entry point for a surgical access device which is inserted into the incision and facilitates the insertion of specialized instruments used in performing surgical procedures within an internal surgical site. The number of incisions may depend on the type of surgery. It is not uncommon for some abdominal operations, e.g., gallbladder surgery, to be performed through a single incision. In most patients, the minimally-invasive approach leads to decreased postoperative pain, shorter hospital stay, faster recovery, decreased incidence of wound-related and pulmonary complications, cost savings by reducing postoperative care, and, in some cases, a better overall outcome.

Minimally-invasive surgical procedures are performed throughout the body and generally rely on obtaining access to an internal surgical site through a relatively small pathway, often less than one centimeter in diameter, to the surgical site. One method of providing such a pathway is by inserting a cannula and trocar assembly through the skin of the patient. Commonly, to place the trocar-cannula, the penetrating tip of the obturator of the trocar is pushed through the skin and underlying tissue until the distal end of the cannula is within the body cavity. Alternatively, some trocar devices have a blunt obturator for placing the cannula through a previously-made incision. Once the trocar has been properly positioned, the obturator is removed and the cannula is then available as a pathway between the surgical site and the exterior of the patient's body through which the surgeon may introduce the various surgical instruments required to perform the desired procedures. Surgical instruments insertable through a cannula include forceps, clamps, scissors, probes, flexible or rigid scopes, staplers and cutting instruments.

In some procedures, a wall of a body cavity is raised by pressurization of the body cavity to provide sufficient working space at the surgical worksite and/or to allow a trocar to penetrate the body cavity without penetrating an organ within the cavity. The process of distending the abdomen wall from the organs enclosed in the abdominal cavity is referred to as insufflation. During a laparoscopic procedure (endoscopy in the abdominal cavity), insufflation is achieved by introducing an insufflation gas, such as carbon dioxide, nitrogen, nitrous oxide, helium, argon, or the like, through a Veress needle or other conduit inserted through the abdominal wall, to enlarge the area surrounding the target surgical site to create a larger, more accessible work area. The surgeon is then able to perform the procedure within the body cavity by manipulating the instruments that have been extended through the surgical access devices. The manipulation of such instruments within the internal body is limited by both spatial constraints and the need to maintain the body cavity in an insufflated state.

In minimally-invasive surgery, the surgeon does not have direct visualization of the surgical field, and thus minimally-invasive techniques require specialized skills compared to the corresponding open surgical techniques. Although minimally-invasive techniques vary widely, surgeons generally rely on a lighted camera at the tip of an endoscope to view the surgical site, with a monitor displaying a magnified version of the site for the surgeon to use as a reference during the surgical procedure. The surgeon then performs the surgery while visualizing the procedure on the monitor. The camera is typically controlled by an assistant to the surgeon who is scrubbed into the procedure. In most instances, the assistant does not play any other role in the procedure other than to hold and direct the camera so that the surgeon can view the surgical site. The camera assistant may have difficulty understanding the surgeon's intent, requiring the surgeon either to move the camera himself or ask the assistant to redirect the camera.

Multi-function robotic surgical systems are available with laparoscopic camera control. In general, robotic surgical systems are large and bulky, requiring a large amount of space around the patient, and have complex, time-consuming setups. Extensive training time is typically required for surgeons to learn to operate the remotely-controlled, camera-toting devices, and additional specialized training is also typically required for the entire operating room team. The extremely high initial cost of purchasing a robotic surgical system as well as the relatively high recurring costs of the instruments and maintenance can make it prohibitive for many hospitals and health-care centers.

SUMMARY

According to an aspect of the present disclosure, a surgical port assembly for use with surgical instruments is provided. The surgical port assembly includes a body including an exterior surface, an interior surface, and an interior space defined by the interior surface. The surgical port assembly includes a control interface including a plurality of drive members coupled to the body and controllable to apply a force to a different portion of a shaft of an surgical instrument, when the shaft is disposed within the interior space, to move a distal portion of the surgical instrument to a desired position within a body cavity.

According to another aspect of the present disclosure, a method of controlling an surgical instrument using a surgical port assembly is provided. The method includes the steps of sensing a position of a distal portion of a surgical instrument, determining whether a button disposed on the surgical instrument is activated, and controlling at least one drive member disposed in association with a body of a surgical port to move a distal portion of an surgical instrument to a position that is aligned with the sensed position of the distal portion of the surgical instrument when it is determined that the button is activated.

BRIEF DESCRIPTION OF THE DRAWINGS

Objects and features of the presently-disclosed methods and apparatus for controlling surgical instruments using a port assembly will become apparent to those of ordinary skill in the art when descriptions of various embodiments thereof are read with reference to the accompanying drawings, of which:

FIG. 7 is a schematic illustration of a surgical system in accordance with another aspect of the present disclosure;

DETAILED DESCRIPTION

Figure 1:
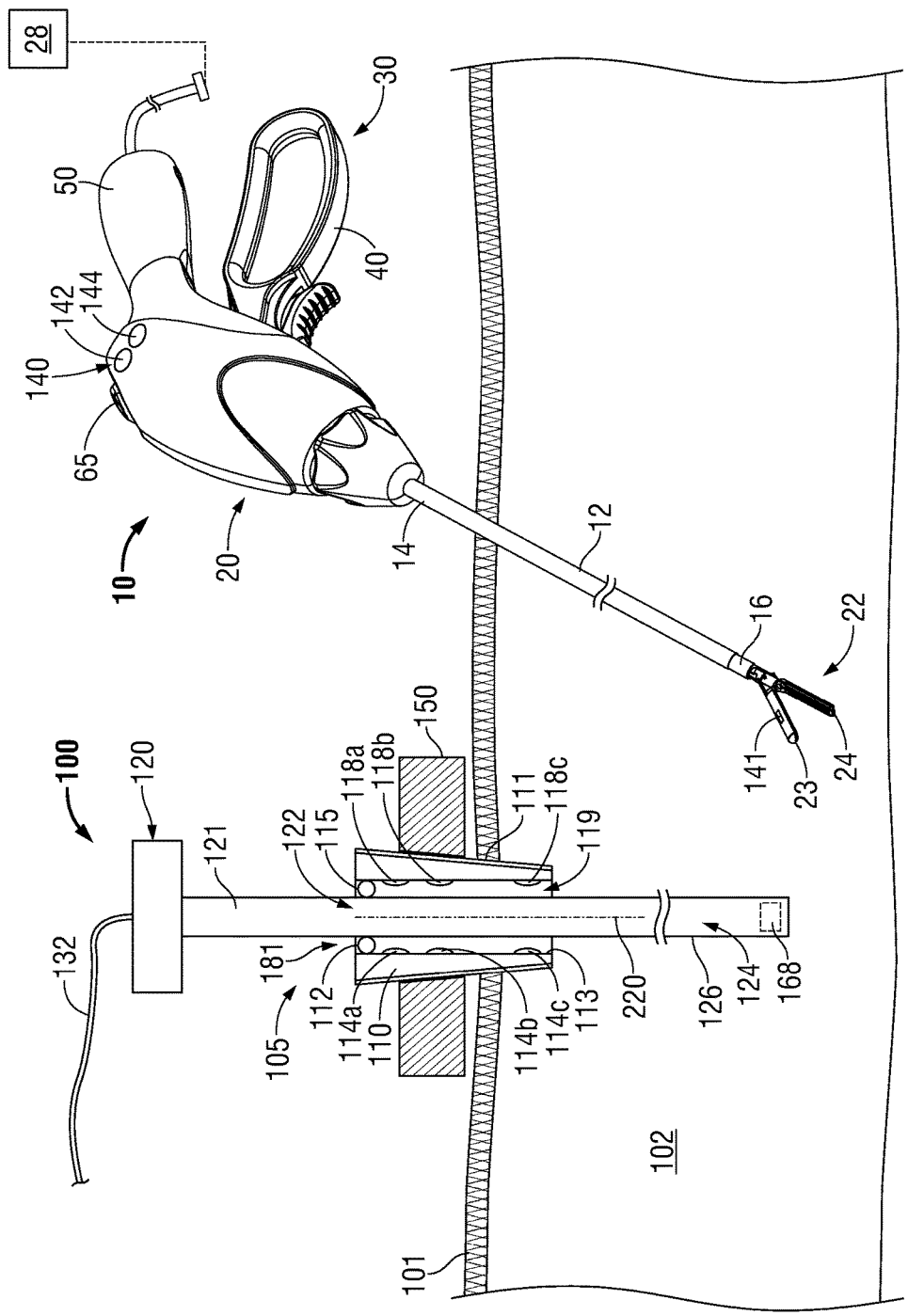
FIG. 1 is a schematic diagram of a system including a bipolar forceps and a port assembly coupled to an endoscopic camera in accordance with an embodiment of the present disclosure.

Hereinafter, embodiments of the presently-disclosed methods and apparatus for controlling surgical instruments using a port assembly are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

A minimally-invasive procedure may be defined as any procedure that is less invasive than open surgery used for the same purpose. As it is used in this description, "endoscopic surgery" is a general term describing a form of minimally-invasive surgery in which access to a body cavity is achieved through several small percutaneous incisions. While endoscopic surgery is a general term, "laparoscopic" and "thoracoscopic" describe endoscopic surgery within the abdomen and thoracic cavity, respectively.

As it is used in this description, "transmission line" generally refers to any transmission medium that can be used for the propagation of signals from one point to another.

Various embodiments of the present disclosure provide a port assembly adapted to hold and control the movement and/or positioning of an surgical instrument, such as, without limitation, an endoscopic camera. Embodiments of the presently-disclosed port assembly may be suitable for use in laparoscopic procedures as well as other minimally-invasive surgical procedures.

Various embodiments of the present disclosure provide an surgical-instrument-and-port-assembly assembly. Embodiments may be used in minimally-invasive procedures, e.g., endoscopic and laparoscopic surgical procedures. Portions of the presently-disclosed surgical-instrument-and-port-assembly assembly may be disposable, replaceable and/or reusable.

Various embodiments of the present disclosure provide a port assembly (also referred to herein as a smart port) wherein control of the movement and/or positioning of a surgical instrument may be performed manually or automatically depending on the preference of the surgeon. In some embodiments, an instrument used in a surgical procedure (also referred to herein as a surgical instrument) may be provided with a user interface including one or more user-actuateable controls and a wireless transmitter to provide a communicative link between the user interface and the port assembly, e.g., to allow the surgeon to change the position and/or orientation of the endoscopic camera.

During minimally-invasive surgical procedures, the working end of an instrument is frequently located near the anatomical structure of interest and/or the surgical site within the working envelop. In some embodiments, wherein automatic control is employed for controlling the movement and/or positioning of an endoscopic camera, a sensor and/or transmitter may be disposed in association with the working end of an instrument, e.g., located on the tip of the instrument, and the endoscopic camera may be automatically controlled to "track" the movement of the instrument tip (e.g., align the field of view of the camera with the working end of the instrument) based on one or more signals outputted by the sensor and/or transmitter. In some embodiments, the sensor and/or transmitter may include an attachment mechanism, e.g., an adhesive backing, to allow the surgeon to selectively position the sensor and/or transmitter on a particular instrument and/or at a particular location on a select instrument, e.g., depending on surgeon preference, the type of surgery, etc.

Some examples of instruments used in minimally-invasive procedures include graspers, cutters, forceps, dissectors, sealers, dividers, or other tools suitable for use in the area of the anatomical structure of interest. The instrument may be a standalone tool suitable for use within a body cavity or external to the patient's body cavity.

In some embodiments, the controls may include an attachment mechanism, e.g., an adhesive backing, to allow the physician to selectively position the controls on a particular instrument and/or at a preferred location on a select instrument. In some embodiments, the capability may be provided to interface with an existing operating-room management system, e.g., using speech recognition technology, to control one or more settings of operating-room equipment. In some embodiments, the port assembly may be a standalone tool that interfaces with any suitable endoscopic camera.

FIG. 1 shows a bipolar forceps 10 and an embodiment of a port assembly 105 coupled to an endoscopic camera 120 according to the present disclosure. Endoscopic camera 120 generally includes an elongated shaft 121 having a distal shaft section 126. In some embodiments, a multi-functional sensor 168 is disposed in association with the distal shaft section 126. In some embodiments, the multi-functional sensor 168 provides illumination and houses a camera chip. It is to be understood that other sensor embodiments may be utilized. Sensor 168 is operably coupled to a power source (e.g., power supply 315 shown in FIG. 3) via a transmission line 132 coupled to the endoscopic camera 120. Although FIG. 1 depicts a bipolar forceps 10 for use in connection with endoscopic surgical procedures, the endoscopic camera 120 and port assembly 105, when operably coupled together (shown generally as 100 in FIG. 1), may be used with a variety of instruments, e.g., depending on the type of surgery.

Port assembly 105 generally includes a body 110 and a control interface 181. Body 110 includes an exterior surface 111, an interior surface 113, and an interior space 119 defined by the interior surface 113. In FIG. 1, the exterior surface 111 of the body 110 is shown disposed in sealable contact with tissue 101 at an entry site into the patient's body cavity 102. Body 110 is adapted to allow access into the body cavity 102, e.g., to allow access of instruments therethrough, and may include sealing elements or mechanisms to seal the opening into the body cavity 102, e.g., to prevent the escape of insufflation gas. Body 110 may be formed of any suitable material such as a metal, alloy, composite material or any combination of such materials.

Control interface 181 includes a plurality of drive members (e.g., drive members 118a, 118b and 118c shown in FIG. 1) coupled to, or otherwise disposed in association with, the body 110. In some embodiments, one or more of the drive members may include an electric motor, e.g., a rotary motor or a linear motor, coupled to the body 110.

In some embodiments, each drive member is controllable to apply a force to a different portion of the shaft 121 of the endoscopic camera 120 (i.e., when the shaft 121, or portion thereof, is disposed within the interior space 119) to move a distal shaft section 126 of the endoscopic camera 120 to a desired position within the body cavity 102. As shown in FIG. 1, a first portion 122 of the shaft 121 of the endoscopic camera 120 may be disposed within the interior space 119 of the body 110 of the port assembly 105, and a second portion 124 of the shaft 121, including the distal shaft section 126, may be disposed within the body cavity 102.

Control interface 181 is adapted to controllably move and/or position the distal shaft section 126 of the endoscopic camera 120 within the body cavity 102. In some embodiments, the control interface 181 may be adapted to receive input signals from a user interface (e.g., user interface 140 disposed in association with the forceps 10 shown in FIG. 1). Based on the input signals, the control interface 181 may adjust the spatial aspects of the endoscopic camera 120 and/or perform other control functions, alarming functions, or other functions in association therewith. Some examples of spatial aspects associated with the endoscopic camera 120 that may be adjusted include tilt angle (e.g., relative to a longitudinal axis of the body 110) and the length of the shaft 121 portion extended into the body cavity 102.

Control interface 181 may be implemented, in conjunction with suitable electronics (e.g., hardware, software or firmware), using a variety of modalities, such as, without limitation, mechanical multi-dimension controlled levers or gears, broader area flexible holders (e.g., multi-chamber) with pneumatic, hydraulic or other actuators that control shape of the holder and the resultant movement and/or control of the endoscopic camera.

Control interface 181 generally includes a plurality of drive members (e.g., 219a-219n and 216a-216n shown in FIG. 2) coupled to the body 110, e.g., disposed in opposing relation to one another. In some embodiments, as shown in FIG. 1, the control interface 181 includes two engagement members 112 and 115 (e.g., roller members) disposed in opposing relation to one another, e.g., adapted to effect upward or downward movement of the shaft 121. In some embodiments, the control interface 181 includes a plurality of engagement members (e.g., six engagement members 118a, 118b, 118c, 114a, 114b and 114c) adapted to change the tilt angle of the shaft 121, e.g., with respect to a longitudinal axis 220 of the body 110. One or more engagement members 118a, 118b, 118c, 114a, 114b and 114c may be configured to apply a force to the shaft 121 in a direction perpendicular to a longitudinal axis 220 of the body 110 and/or perpendicular to a longitudinal axis of the port assembly 105.

In some embodiments, one or more first drive members are coupled to a first side of the body 110 along a longitudinal axis of the port assembly 105 and adapted to impart reciprocalable movement to one or more engagement members (e.g., three engagement members 114a, 114b and 114c), and one or more second drive members are coupled to a second side of the body 110 along a longitudinal axis of the port assembly 105 and adapted to impart reciprocalable movement to one or more engagement members (e.g., three engagement members 118a, 118b and 118c). The one or more first drive members and the one or more second drive members may form a set of drive members, wherein the set of drive members may be configured to operate in coordination to change the position of the distal shaft section 126 of the endoscopic camera 120.

In some embodiments, as shown in FIG. 1, the port assembly 105 is coupled to a holding member 150. Holding member 150 may be adapted to be attachable to a table to provide support for the port assembly 105, e.g., to provide additional stability and/or reduce the weight of the tool on the patient's body. Although FIG. 1 depicts an endoscopic camera 120, the port assembly 105 may be used with a wide variety of surgical instruments or other tools having a shaft suitably configured to be receivable within the interior space 119 of the port assembly 105.

In FIG. 1, an embodiment of an endoscopic bipolar forceps 10 is shown for use with various surgical procedures and generally includes a housing assembly 20, a handle assembly 30, and an end-effector assembly 22. Forceps 10 includes a shaft 12 that has a distal end 16 configured to mechanically engage the end-effector assembly 22 and a proximal end 14 configured to mechanically engage the housing assembly 20. End-effector assembly 22 generally includes a pair of opposing jaw assemblies 23 and 24 pivotably mounted with respect to one another. As can be appreciated, squeezing the movable handle 40 toward the fixed handle 50 pulls a drive sleeve (not shown) proximally to impart movement to the jaw assemblies 23 and 24 from an open position, wherein the jaw assemblies 23 and 24 are disposed in spaced relation relative to one another, to a clamping or closed position, wherein the jaw assemblies 23 and 24 cooperate to grasp tissue therebetween.

A transmission line operably connects the forceps 10 to an electrosurgical power generating source 28. Forceps 10 may alternatively be configured as a wireless device or battery-powered. Forceps 10 includes a switch 65 configured to permit the user to selectively activate the forceps 10. When the switch 65 is depressed, electrosurgical energy is transferred through one or more electrical leads (not shown) to the jaw assemblies 23 and 24.

In some embodiments, as shown in FIG. 1, the forceps 10 includes a user interface 140, which may be adapted to provide a wireless communication interface with the control interface 181 of the port assembly 105. Additionally, or alternatively, the forceps 10 may include a sensor and/or transmitter 141, e.g., disposed in association with the end effector assembly 22, or component thereof, e.g., jaw assembly 23.

User interface 140 may be disposed on another part of the forceps 10 (e.g., the fixed handle 50, etc.) or another location on the housing assembly 20. User interface 140 may include one or more controls (e.g., two controls 142 and 143 shown in FIG. 1), which may include a switch (e.g., pushbutton switch, toggle switch, slide switch) and/or a continuous actuator (e.g., rotary or linear potentiometer, rotary or linear encoder). In some embodiments, the user interface 140 includes a first control (e.g., control 142) adapted to transmit signals indicative of user intent to effect upward or downward movement of the endoscopic camera 120 within the body cavity 102, e.g., used for controlling the drive members 112 and 115. User interface 140 may additionally, or alternatively, include a second control (e.g., control 143) adapted to transmit signals indicative of user intent to adjust the tilt angle of the endoscopic camera 120, e.g., used for controlling the movement of the engagement members 118a, 118b, 118c, 114a, 114b and 114c.

In some embodiments, the control interface 181 of the port assembly 105 is communicatively coupled to the sensor and/or transmitter 141. Control interface 181 may include a receiver (e.g., receiver 339 shown in FIG. 3), and may be adapted to controllably move and/or position the distal shaft section 126 of the endoscopic camera 120 within the body cavity 102 using one or more electrical signals received from the sensor and/or transmitter 141. In some embodiments, the user interface 140 includes a first control (e.g., control 142) adapted to transmit signals indicative of user intent to activate an automatic-control mode of operation of the port assembly 105 to automatically align the field of view of the camera with the working end of a surgical instrument (e.g., forceps 10) based on one or more signals outputted by the sensor and/or transmitter 141, and may include a second control (e.g., control 143) adapted to transmit signals indicative of user intent to deactivate the automatic-control mode of operation.

Figure 2:
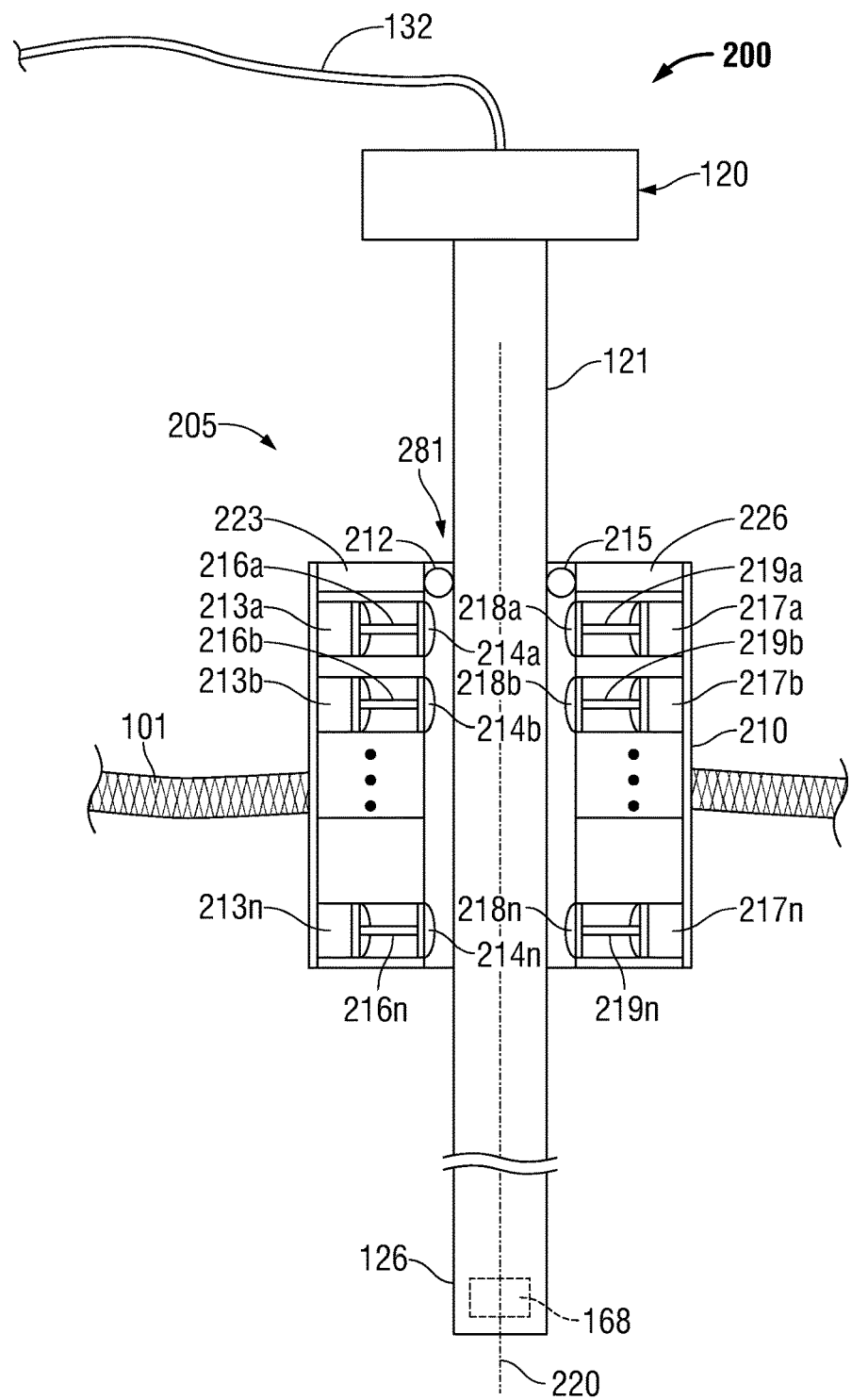
FIG. 2 is a schematic diagram of a port assembly coupled to the endoscopic camera shown in FIG. 1 in accordance with an embodiment of the present disclosure.

FIG. 2 shows an embodiment of a port assembly 205 coupled to the endoscopic camera 120 of FIG. 1. Port assembly 205 generally includes a body 210 and a control interface 281. Control interface 281 generally includes a plurality of drive members operably coupled to a plurality of drivers.

As shown in FIG. 2, the control interface 281 includes two drive members 212 and 215 disposed in opposing relation to one another at the proximal end of the body 210 and operably coupled to two drivers 223 and 226, respectively. Drivers 223 and 226 may include an electric motor coupled to the body 210. In some embodiments, the drivers 223 and 226 may be adapted to impart rotational movement to the drive members 212 and 215, respectively, e.g., to effect upward or downward movement of the shaft 121 and/or to translate the endoscopic camera 120 along a longitudinal axis thereof. In some embodiments, each of the drive members 212 and 215 includes a roller member, and the drivers 223 and 226 may include rotary motors mechanically coupled to the roller members.

Control interface 281 includes a plurality of drive members 219a-219n and 216a-216n operably coupled to drivers 217a-217n and 213a-213n, respectively. In some embodiments, the control interface 281 may include a plurality of engagement members 218a-218n and 214a-214n operably coupled to the drive members 219a-219n and 216a-216n, respectively. In some embodiments, the drive members 219a-219n and the engagement members 218a-218n, respectively, may be integrally formed unitary structures, and/or the drive members 216a-216n and the engagement members 214a-214n, respectively, may be integrally formed unitary structures.

In some embodiments, the drivers 217a-217n and 213a-213n are adapted to impart reciprocalable movement to the drive members 219a-219n and 216a-216n, respectively, e.g., to change the tilt angle of the shaft 121, e.g., with respect to a longitudinal axis 220 of the body 210. Drivers 217a-217n and 213a-213n and/or the drive members 219a-219n and 216a-216n may additionally, or alternatively, be adapted to impart reciprocalable movement to the engagement members 218a-218n and 214a-214n, respectively, e.g., to change the tilt angle (e.g., angle 321 shown in FIG. 3) of the shaft 121.

Control interface 281 may include a receiver (e.g., receiver 339 shown in FIG. 3), and may be adapted to controllably move and/or position the distal shaft section 126 of the endoscopic camera 120 using on one or more electrical signals received from a sensor and/or transmitter (e.g., sensor and/or transmitter 141 shown in FIG. 1) disposed in association with an instrument. Endoscopic camera 120 and the port assembly 205, when operably coupled together (shown generally as 200 in FIG. 2), may be suitable for use in connection with a variety of procedures involving different instruments, e.g., bipolar forceps 10 of FIG. 1.

Figure 3:
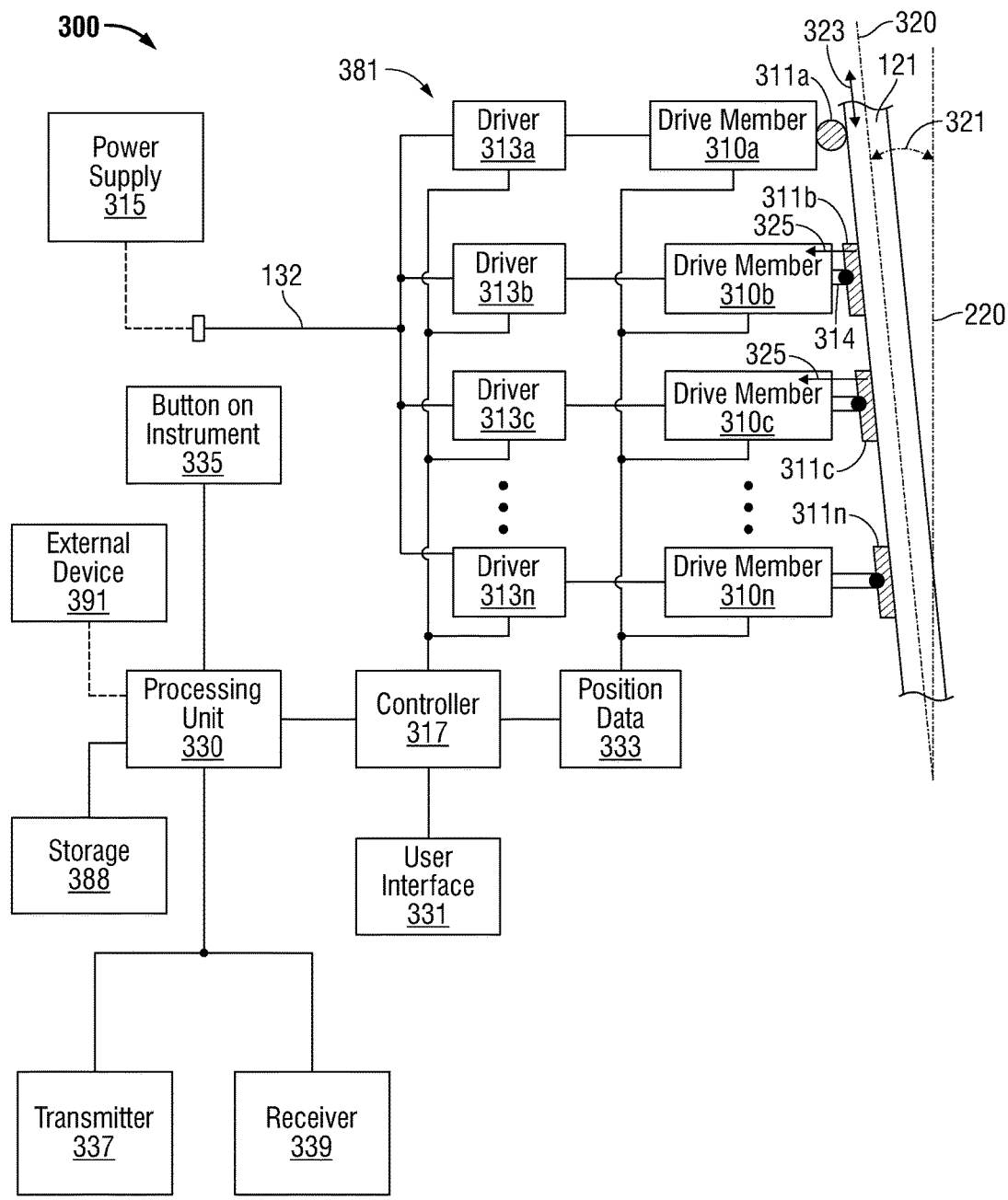
FIG. 3 is a block diagram of a system including a control interface of a port assembly shown coupled to a portion of the shaft of the endoscopic camera shown in FIGS. 1 and 2 in accordance with an embodiment of the present disclosure.

FIG. 3 illustrates a functional block diagram of a system 300 including an embodiment of a control interface 381 operably coupled to a portion of the shaft 121 of the endoscopic camera 120 (shown in FIGS. 1 and 2). Control interface 381, or portions thereof, may be used with one or more of the presently-disclosed port assembly embodiments, e.g., port assembly 118 shown in FIG. 1, or port assembly 218 shown in FIG. 2.

System 300 includes a plurality of drive members 310a-310n, a plurality of drivers 313a-313n coupled to the drive members 310a-310n, respectively, a controller 317 communicatively coupled to the drivers 313a-313n, and a user interface 331 communicatively coupled to the controller 317. System 300 may additionally include a plurality of engagement members 311a-311n coupled to the drive members 310a-310n, respectively. In some embodiments, during operation of the control interface 381 to move and/or position the distal shaft section 126 of the endoscopic camera 120 within the body cavity 102 (shown in FIG. 1), one or more of the engagement members 311a-311n may be actuated to apply force to one or more different portions of the shaft 121.

System 300 includes a power supply 315. Drivers 313a-313n may be electrically coupled via a transmission line 132 to the power supply 315. The various components in the system 300 may be electrically coupled by one or more signal lines or communication buses of one form or another.

Controller 317 is configured to generate one or more electrical signals for controlling operation of one or more components of the system 300, and may be configured to use position data 333 received from the drive members 310a-310n. Controller 317 may be configured to generate one or more electrical signals for controlling one or more of the drivers 313a-313n, which, in turn, may transmit one or more electrical signals to one or more of the drive members 310a-310n for actuating one or more of the engagement members 311a-311n to apply force to the shaft 121.

In some embodiments, the shaft 121 may be disposed within an interface member (e.g., inner tubular member 505 shown in FIG. 5) configured to interface with the shaft 121 to form a seal between the port assembly and the shaft 121, wherein one or more of the engagement members 311a-311n may be disposed in contact with the interface member.

In some embodiments, responsive to one or more electrical signals received from the controller 317, the driver 313a and/or the drive member 310a may be adapted to impart rotational movement to the engagement member 311a, e.g., to effect upward and/or downward movement 323 of the shaft 121 and/or to translate the endoscopic camera 120 along a longitudinal axis thereof. In some embodiments, responsive to one or more electrical signals received from the controller 317, the drivers 313b-313n and/or the drive members 310b-310n may be adapted to impart reciprocalable movement to the engagement members 311a-311n, respectively, e.g., to change the tilt angle 321 of the shaft 121. As shown in FIG. 3, the tilt angle 321 may be defined with respect to a longitudinal axis 320 of the shaft 121 and a longitudinal axis 220 of the body (e.g., body 110 shown in FIG. 1, or body 210 shown in FIG. 2) of the port assembly.

System 300 may include a storage device 388. Storage device 388 may include a set of executable instructions for performing a method of controlling surgical instruments using a port assembly as described herein In some embodiments, as shown in FIG. 3, the system 300 includes a processing unit 330.

Processing unit 330 may include any type of computing device, computational circuit, or any type of processor or processing circuit capable of executing a series of instructions that are stored in a memory, e.g., storage device 388 and/or external device 391. In some embodiments, the user interface 331 may be communicatively coupled to the processing unit 330. Processing unit 330 and the controller 317 may be separate components or may be integrated, such as in one or more integrated circuits. In some embodiments, processing unit 330 may be configured to execute a set of programmed instructions for performing the functionality of the controller 317. Processing unit 330 may additionally, or alternatively, be configured to execute a set of programmed instructions for performing a method of controlling surgical instruments using a port assembly as disclosed herein.

System 300 may also include a database (not shown) communicatively coupled to the processing unit 330 and configured to store and retrieve data, e.g., transmitter 337 identification information associated with one or more surgical instruments (e.g., forceps 10 shown in FIG. 1). The database may be maintained at least in part by data provided by an external device 391.

Figure 4:
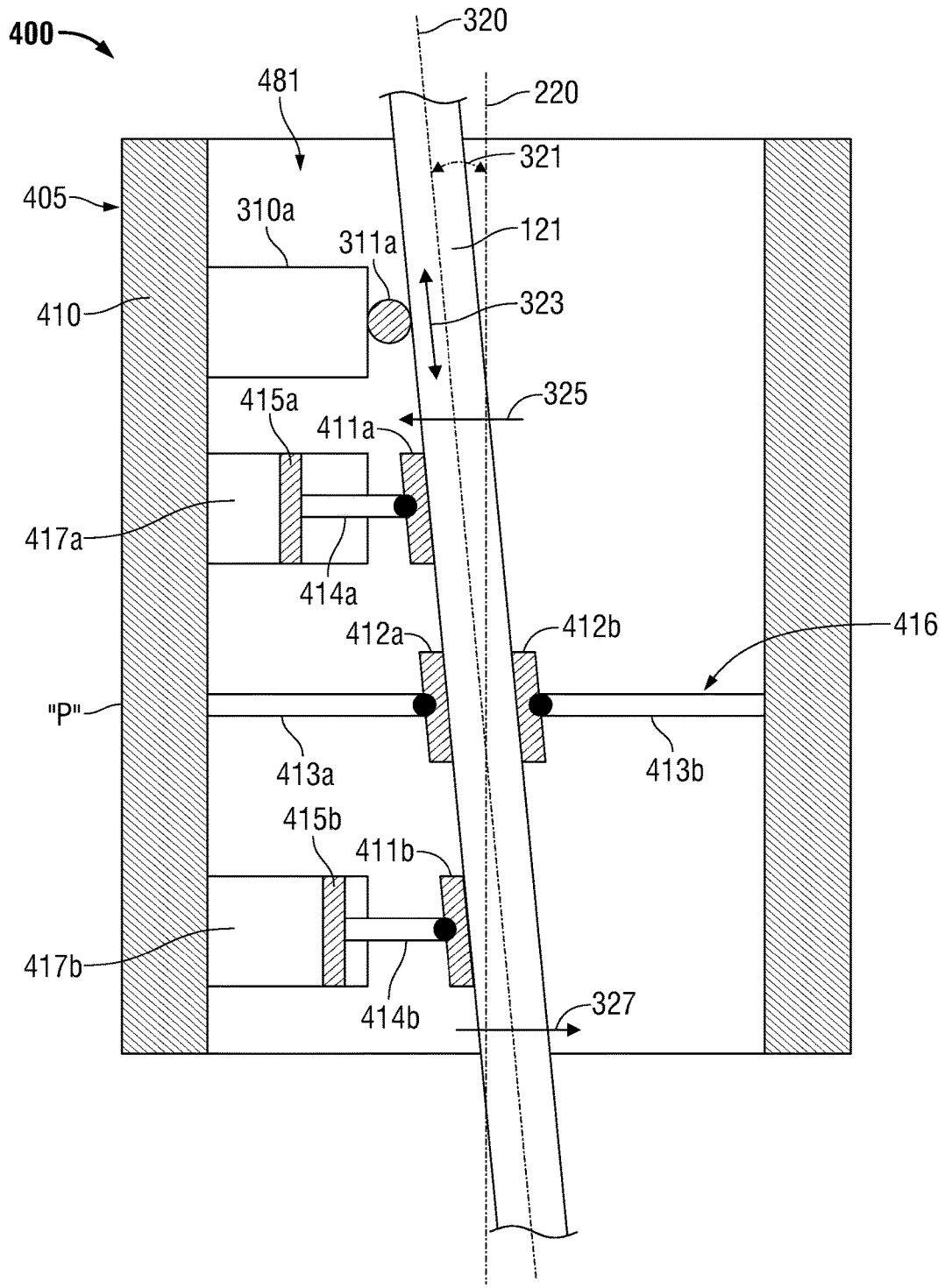
FIG. 4 is a schematic diagram of a portion of a port assembly coupled to the endoscopic camera shown in FIG. 1 in accordance with an embodiment of the present disclosure.

FIG. 4 shows a portion of a port assembly 405 according to an embodiment of the present disclosure that is operably coupled to a portion of the shaft 121 of the endoscopic camera 120 shown in FIGS. 1 and 2. Port assembly 405 generally includes a body 410 and a control interface 481. Port assembly 405 includes a retaining member 416 configured to hold the shaft 121 at a position "P" within the body 410. In some embodiments, the position "P" may be located at the midpoint of the length of the body 410.

Retaining member 416 is configured to provide stability to the shaft 121 and allow upward and/or downward movement 323 of the shaft 121. In some embodiments, as shown in FIG. 4, the retaining member 416 includes two arm members 413a and 413b disposed in opposing relation to one another. Arm members 413a and 413b include a first end and a second end. Arm members 413a and 413b are coupled to the body 410 at the first ends thereof. Retaining member 416 may include two engagement members 412a and 412b disposed at the second ends of the arm members 413a and 413b, respectively. In some embodiments, the engagement members 412a and 412b are disposed in contact with the shaft 121 and configured to allow the shaft to be slideably moveable therebetween. Although one retaining member is shown in FIG. 4, it is to be understood that the port assembly 405 may include any suitable configuration of one or more retaining members disposed at one or more positions within the body 410.

Control interface 481 generally includes a plurality of drive members operably coupled to a plurality of drivers. In some embodiments, as shown in FIG. 4, the control interface 481 includes the drive member 310a and the engagement member 311a shown in FIG. 3. Drive member 310a may be adapted to impart rotational movement to the engagement member 311a, e.g., to effect upward and/or downward movement 323 of the shaft 121. Control interface 481 includes two drivers 417a and 417b and two drive members 414a and 414b operably coupled to the drivers 417a and 417b, and may include two engagement members 411a and 411b operably coupled to the drive members 414a and 414b, respectively. In some embodiments, the drive members 414a and 414b may be adapted to impart reciprocalable movement to the engagement members 411a and 411b, respectively, e.g., to change the tilt angle 321 of the shaft 121. In some embodiments, as shown in FIG. 4, the drivers 417a and 417b include a piston 415a and 415b, respectively, operably coupled to the drive members 414a and 414b, respectively. Drivers 417a and/or the driver 417b may include a pressurized fluid chamber, wherein the piston 415a and/or the piston 415b is disposed in association with the pressurized fluid chamber.

Port assembly 405 may include one or more of the components of the system 300 shown in FIG. 3. Endoscopic camera 120 and the port assembly 405, when operably coupled together (shown generally as 400 in FIG. 4), may be suitable for use in connection with a variety of procedures involving different instruments, e.g., bipolar forceps 10 of FIG. 1.

Figure 5:
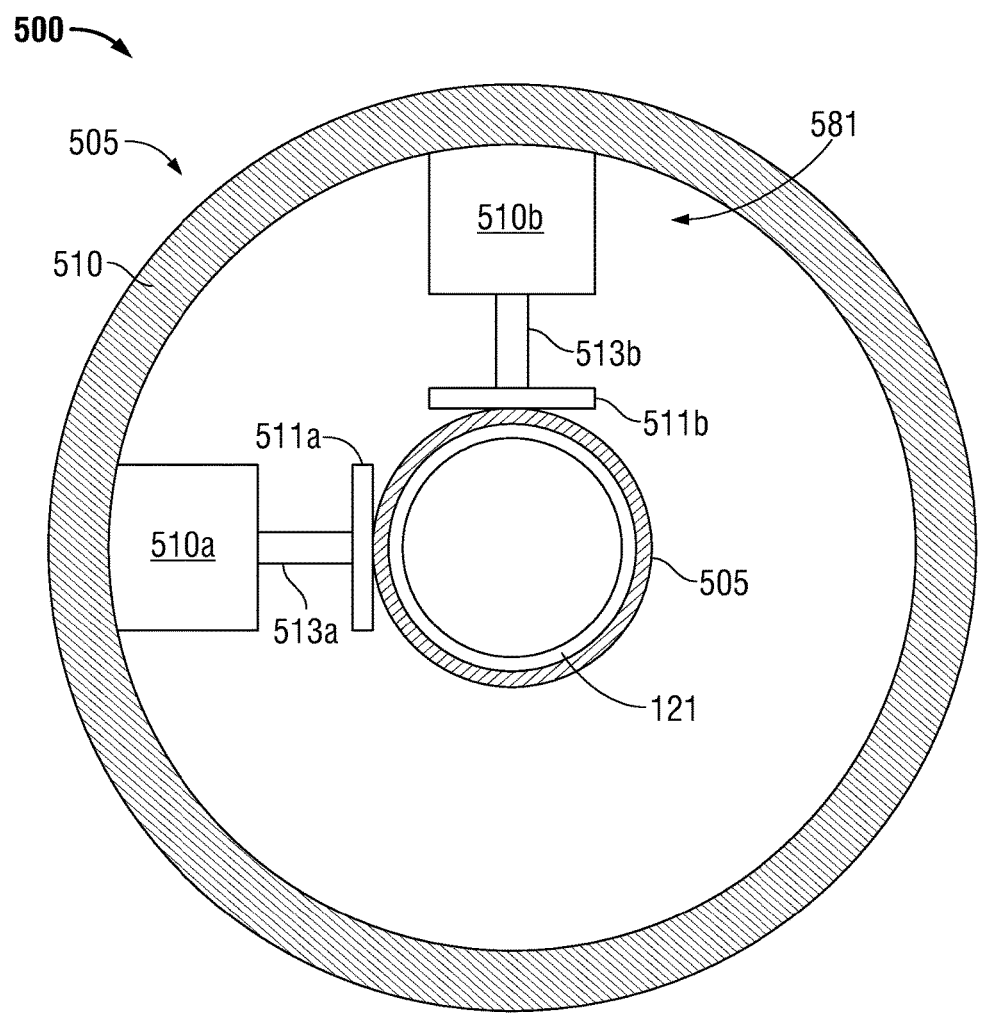
FIG. 5 is a schematic diagram of a portion of a port assembly coupled to the endoscopic camera shown in FIG. 1 in accordance with another embodiment of the present disclosure.

FIG. 5 shows a portion of a port assembly 505 according to an embodiment of the present disclosure that is operably coupled to a portion of the shaft 121 of the endoscopic camera 120 shown in FIGS. 1 and 2. Port assembly 505 includes a body 510, a control interface 581, and a flexible, inner tubular member 505.

Control interface 581 generally includes a plurality of drivers operably coupled to a plurality of drive members. In some embodiments, as shown in FIG. 5, the shaft 121 is disposed within a flexible, inner tubular member 505, and two engagement members 511a and 511b are disposed in contact with the inner tubular member 505. Control interface

581 includes two drivers 510a and 510b and two drive members 513a and 513b operably coupled to the drivers 510a and 510b. Drive members 513a and 513b are operably coupled to the engagement members 511a and 511b.

In some embodiments, the drive members 513a and 513b may be adapted to impart reciprocable movement to the engagement members 511a and 511b, respectively, e.g., to change the tilt angle 321 (shown in FIGS. 3 and 4) of the shaft 121 and/or to move a distal shaft section 126 (shown in FIG. 1) to a desired position within the body cavity 102.

Control interface 581 may include one or more components of the control interface 381 shown in FIG. 3, e.g., the drive member 310a and the engagement member 311a, the controller 317, and/or the processing unit 330. Port assembly 505 may additionally, or alternatively, include one or more components of any of the presently-disclosed port assembly embodiments (e.g., port assembly 105 shown in FIG. 1, port assembly 205 shown in FIG. 2, or port assembly 405 shown in FIG. 4).

Hereinafter, a method of controlling surgical instruments using a port assembly, in accordance with the present disclosure, is described with reference to FIG. 6. It is to be understood that the steps of the method provided herein may be performed in combination and in a different order than presented herein without departing from the scope of the disclosure.

Figure 6:
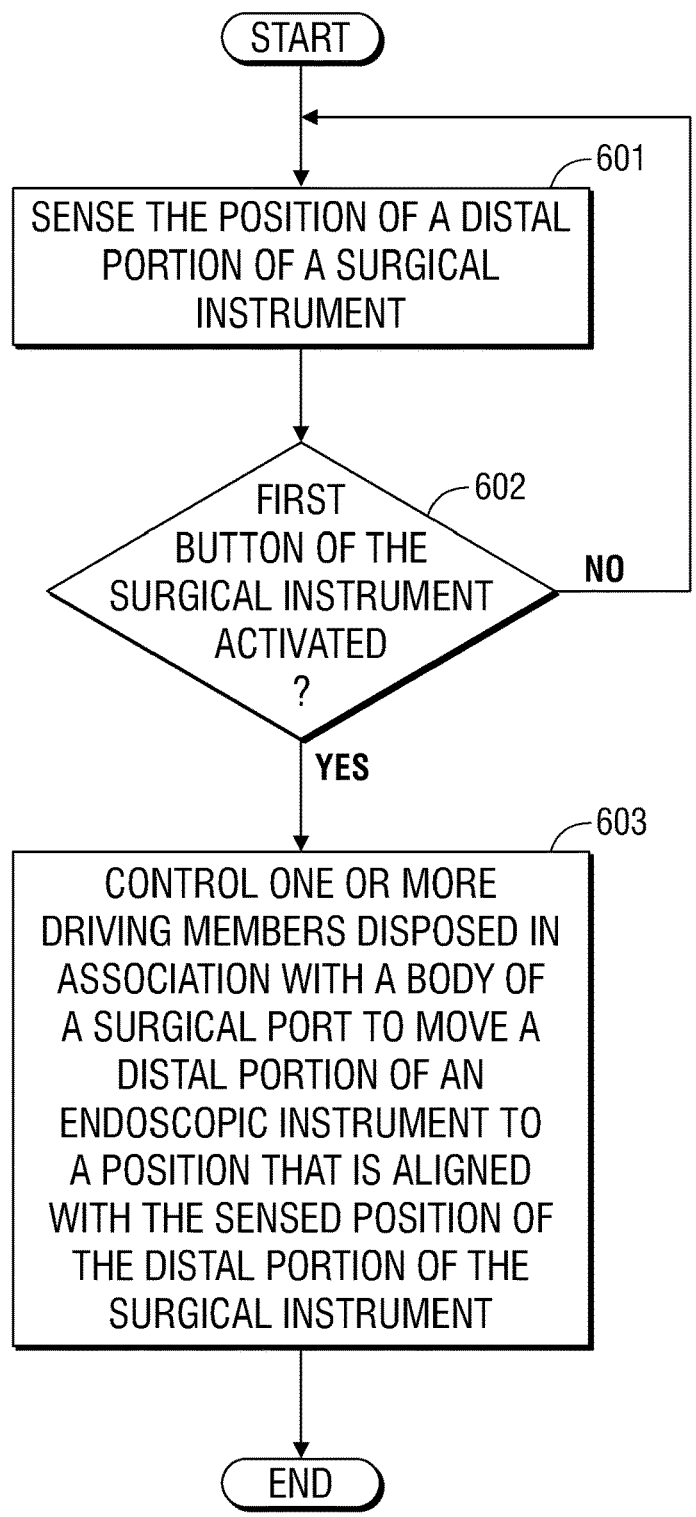
FIG. 6 is a flowchart illustrating a method of controlling surgical instruments using a port assembly in accordance with an embodiment of the present disclosure.

FIG. 6 is a flowchart illustrating a method of controlling surgical instruments using a port assembly according to an embodiment of the present disclosure. In step 610, the position of a distal portion of a surgical instrument 10 is sensed. In some embodiments, sensing the position of the distal portion of the surgical instrument 10, in step 610, may include sensing the signal transmitted from a transmitter 141 disposed on a distal portion of the surgical instrument 10.

In step 620, a determination is made whether a button 142 disposed on the surgical instrument 10 is activated.

If it is determined that the button 142 is activated, in step 620, then, in step 630, one or more drive members 219a-219n and 216a-216n disposed in association with a body 210 of a surgical port assembly 205 are used to move a distal portion 126 of the endoscopic camera 120 to a position that is aligned with the sensed position of the distal portion of the surgical instrument 10. In some embodiments, controlling the surgical port assembly 205 to move the distal portion 126 of the endoscopic camera 120 to another position based on the position of the distal portion of the surgical instrument 10, in step 630, includes controlling the surgical port assembly 205 to move the distal portion of the endoscopic camera 120 to another position based on the signal transmitted from the transmitter 141.

FIG. 7 shows a surgical robotic system 1000. Robotic system 1000 may include two or more supporting arms 1002, 1003, each attached to a respective port assembly 405; a control device 1004; and an operating console 1005 coupled with control device 1004. Supporting arms 1002, 1003 may be robotically moving arms or they may be manually adjusted. Supporting arms 1002, 1003 may be coupled to their respective port assemblies 405 to hold the port assemblies 405 in a predetermined fixed position during surgery to prevent unintentional movement of the port assembly 405 during the surgical procedure. In some instances one or more of the supporting arms 1002, 1003 may be affixed to the operating table 1012 supporting the patient 1013 or they may be affixed to another steady supporting object such as a wall, ceiling, or moveable cart located near the patient table 1012.

Operating console 1005 may include a display device 1006, which is set up in particular to display two- and/or three-dimensional images obtained from an image capture device inserted into the patient; and manual input devices 1007, 1008, by means of which a person (not shown), for example a surgeon, is able to telemanipulate one or more components of the surgical system 1000. For example, in some instances the person may be able to telemanipulate one or more components in a port assembly 405 to manipulate a surgical instrument 1400 inserted in the port assembly 405. The person may also be able to telemanipulate supporting arms 1002, 1003 (to the extent that the arms 1002, 1003 are robotic) in some instances. The person may also be able to telemanipulate other components in the surgical instrument, such as opening and closing a grasper affixed to the end of a surgical instrument inserted into the port assembly 405 via a drive unit coupled to the component in the surgical instrument.

Each of the supporting arms 1002, 1003 may include two or more members connected through joints. One or more of the members or joints may be manually and/or robotically adjustable. System 1000 may also include one or more drive units. A drive unit may drive one or more of the joints or members in the supporting arms 1002, 1003. A drive unit may drive one or more components in the port assembly 405 to manipulate the position and/or orientation of a surgical instrument 1400 inserted into the port assembly 405. A drive unit may drive one or more components in the surgical instrument 1400 to manipulate a component, such as an end effector, that is part of the surgical instrument 1400.

Control device 1004 (e.g., a computer) may be set up to activate one or more of the drive units, in particular by means of a computer program, in such a way that the supporting arms 1002, 1003; components of the port assemblies 405; and/or components of the surgical instruments 1400 (such as an end effector) execute a desired movement according to a movement defined by means of manual input devices 1007, 1008. Control device 1004 may also be set up in such a way that it regulates the movement of robotic arms 1002, 1003 and/or surgical instruments 1400 in the port assemblies 405.

Surgical system 1000 may be configured for use on a patient 1013 lying on a patient table 1012 to be treated in a minimally invasive manner by means of an end effector. Surgical system 1000 may also include more than two supporting arms 1002, 1003 and port assemblies 405, the additional arms likewise being connected to control device 1004 and being telemanipulatable by means of operating console 1005. Similar or different surgical instruments 1400 may be inserted in one or more of the port assemblies 405. Surgical instruments 1400 may further include an elongate body or tube 1404 supporting an end effector that may be configured for performing one or more surgical functions.

Control device 1004 may control a drive unit such as a motor that may be configured to drive a pushing or a pulling of a cable or rod (not shown) extending between an end effector of surgical instrument 1400 and a respective driven member of surgical instrument 1400, as described herein. In use, as cables or rods may be pushed or pulled relative to end effector, cables or rods effect operation and/or movement of each end effector of a surgical instrument 1400. It is contemplated that control device 1004 coordinates the activation of the various motors to coordinate a pushing or a pulling motion of a respective cable in order to coordinate an operation and/or movement of a respective end effector of a surgical instrument 1400. In embodiments, each motor may be configured to actuate a drive rod or a lever arm to effect operation and/or movement of each end effector of surgical instrument 1400.

Figure 8C:
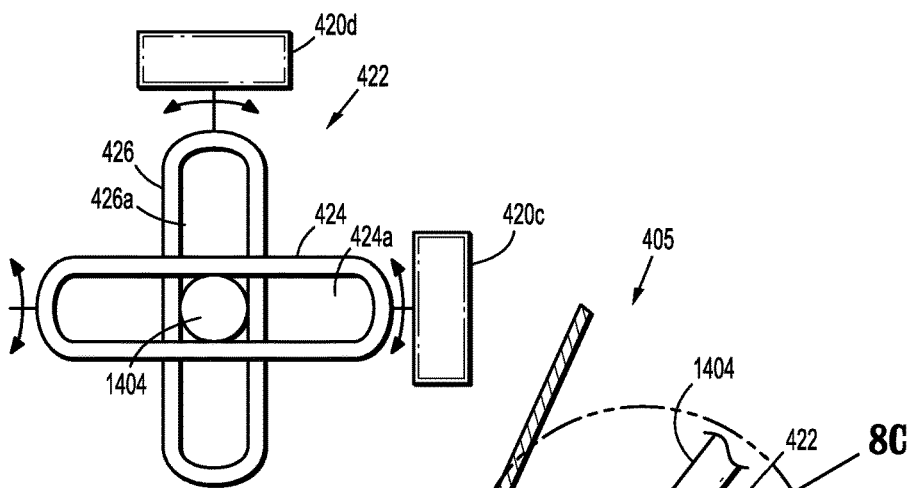
FIG. 8C is an enlarged schematic illustration of the indicated area of detail of FIG. 8A.
Figure 8A:
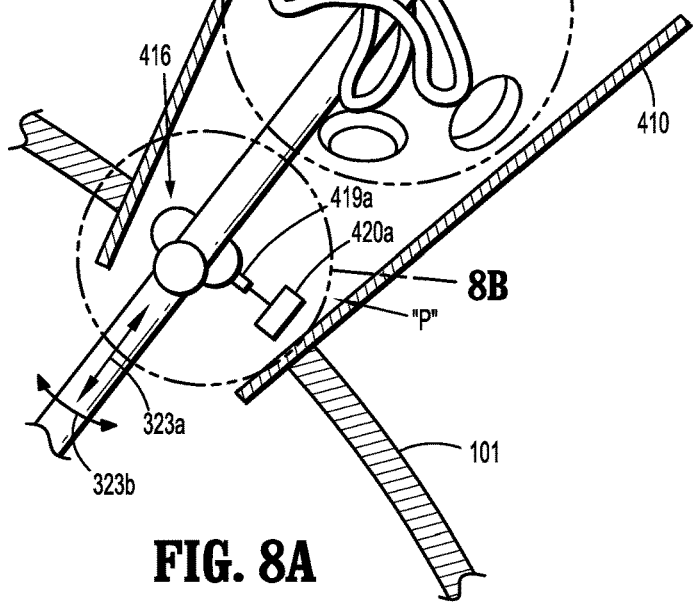
FIG. 8A is a schematic illustration of port assembly according to another embodiment of the present disclosure, shown with an elongate surgical instrument shaft extending therethrough.
Figure 8B:
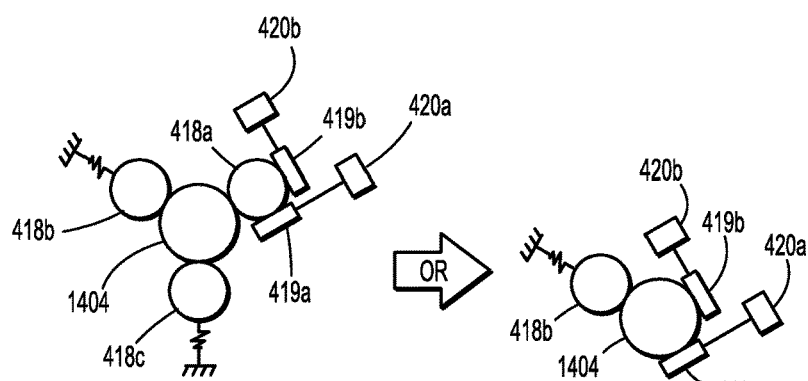
FIG. 8B is an enlarged schematic illustration showing two different exemplary configurations of the indicated area of detail of FIG. 8A.

FIGS. 8A-8C show an exemplary configuration of a port assembly 405. Port assembly 405 may include a retaining mechanism 416 configured to hold elongate body 1404 of surgical instrument 1400 at a pivot location or position "P" within the body 410 of port assembly 405. In some embodiments, the position "P" may be located co-planar with, in parallelism with or in close proximity to tissue 101.

Retaining mechanism 416 may be configured to provide stability to elongate body 1404 of surgical instrument 1400, to allow upward and/or downward movement 323a of elongate body 1404 about a longitudinal axis thereof, and rotational movement 323b of elongate body 1404 about the longitudinal axis thereof.

In some embodiments, as shown in FIGS. 8A and 8B, the retaining mechanism 416 may include at least three equally, radially spaced apart balls 418a, 418b, and 418c. Other embodiments may include less than three balls provided that the elongate body 1404 is still adequately supported by another object(s). Balls 418a-418c may be biased toward one another, such as by springs or the like. Each ball 418a-418c may be rotatably supported in body 410 of port assembly 405 so as to be able to rotate freely therewithin. Each ball 418a-418c may be supported in body 410 of port assembly 405 so as to be at a fixed location along a length of port assembly 405.

At least one ball 418a, 418b or 418c of balls 418a-418c may be motorized or driven, while the remaining ball(s) 418a-418c remain passive. For example, a first ball 418a may be driven by a pair of motorized rollers 419a, 419b that are each in contact with a surface of first ball 418a. Each roller 419a, 419b may be driven by a respective motor 420a, 420b.

In some instances, two or more of the balls 418a, 418b, and 418c may be motorized. Each of the motorized balls 418a, 418b, and/or 418c may be driven by a pair of respective motorized rollers similar to rollers 419a and 419b. In some instances, one of the motorized balls 418a, 418b, or 418c may be actuated about a first axis and another of the motorized balls 418a, 418b, or 418c may be actuated about a second axis different from the first axis. The second axis may be perpendicular to the first axis.

In operation, depending on a relative actuation of motors 420a, 420b, and in turn rollers 419a, 419b, first ball 418a may be spun or rotated to effectuate longitudinal movement 323a of elongate body 1404 of surgical instrument 1400 about a longitudinal axis thereof and/or rotational movement 323b of elongate body 1404 of surgical instrument 1400 about the longitudinal axis thereof.

In other embodiments, such as shown in the second of two exemplary alternative configurations in FIG. 8B, one or more of the balls may be removed and one or more of the motorized rollers 419a, 419b may directly contact the elongate body 1404 of surgical instrument 1400 to allow upward and/or downward movement 323a of elongate body 1404 about a longitudinal axis thereof, and rotational movement 323b of elongate body 1404 about the longitudinal axis thereof depending on how the respective motors 420a, 420b are actuated.

With continued reference to FIGS. 8A-8C, port assembly 405 may further include a pivoting mechanism 422 configured to pivot elongate body 1404 of surgical instrument 1400 about pivot location or position "P" within the body 410 of port assembly 405.

In some embodiments, as shown in FIGS. 8A and 8C, the pivoting mechanism 422 may include a pair of cam plates 424, 426 overlaying one another. Each plate 424, 426 may be arcuate or curved. Each plate 424, 426 may define an elongate slot 424a, 426a therein, wherein elongate slots 424a, 426a intersect one another.

Each plate 424, 426 may be supported in body 410 of port assembly 405 so as to be translatable therewithin. Each plate 424, 426 may be supported in body 410 of port assembly 405 so as to be at a fixed location along a length of port assembly 405 and pivoting mechanism 422 may be spaced at an axial distance from retaining mechanism 416.

Each plate 424, 426 may be translated axially by a respective motor 420c, 420d that is threadingly connected to plate 424, 426 by a rotatable shaft. In use, as each plate is axially translated, relative to one another, an intersecting point of each slot 424a, 426a formed therein may be relocated relative to a central axis of body 410 of port assembly 405.

In some instances, each plate may be in the form of a disc with each disc defining an elongate linear or arcuate slot formed therein. The pair of discs may be parallel to one another and may be independently rotatable relative to one another, about a central pivot axis thereof, such as by a respective motor or the like. The central axis of each is co-linear with the central axis of body 410 of port assembly 405. In use, as each plate is rotated about its central pivot axis, relative to one another, an intersecting point of each slot formed therein may be relocated relative to the central axis of body 410 of port assembly 405. With elongate body 1404 of surgical instrument 1400 extending through the intersecting point of the slot of each disc, as the discs are rotated relative to one another, about the central pivot axis thereof, elongate body 1404 of surgical instrument 1400 may be pivoted relative to the central axis of body of port assembly 405.

In operation, with elongate body 1404 of surgical instrument 1400 passing through each slot 424a, 426a of plates 424, 426, depending on a relative actuation of motors 420c, 420d, and in turn the relative intersection point of slots 424a, 426a of plates 424, 426, elongate body 1404 of surgical instrument 1400 may be tilted or pivoted relative to pivot point "P".

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical port assembly for use with surgical instruments, comprising:
a body including an exterior surface and an interior space defined by an interior surface of the body, the body defining a longitudinal axis; and
a control interface including a plurality of drive members coupled to the body, at least one drive member including an arm and an engagement member supported on the arm, the engagement member positionable at an angle relative to the arm and the longitudinal axis of the body, the engagement member positioned to move linearly in a direction that extends across the longitudinal axis of the body to apply a linear force to a first portion of a shaft of a surgical instrument, when the shaft is disposed within the interior space, and to selectively tilt the surgical instrument away from the longitudinal axis to move a distal portion of the surgical instrument to a desired position within a body cavity.

2. The surgical port assembly of claim 1, wherein the at least one drive member is configured to apply the linear force to the surgical instrument in a direction perpendicular to the longitudinal axis of the body.

3. The surgical port assembly of claim 1, further comprising an interface member coupled to the plurality of drive members, the interface member configured to interface with the surgical instrument to form a seal between the surgical port assembly and the surgical instrument.

4. The surgical port assembly of claim 1, wherein the control interface further includes a plurality of drivers, at least one of the plurality of drivers including an electric motor coupled to the body, wherein at least one of the plurality of drive members is operatively coupled to the electric motor, the electric motor configured to drive the at least one drive member to apply force to the surgical instrument when the surgical instrument is placed in the surgical port assembly.

5. The surgical port assembly of claim 4, wherein at least one of the plurality of drivers includes a pressurized fluid chamber, at least one of the plurality of drive members operatively coupled to the pressurized fluid chamber, the pressurized fluid chamber configured to drive the drive member to apply force to the surgical instrument when the surgical instrument is placed in the surgical port assembly.

6. The surgical port assembly of claim 1, wherein the plurality of drive members include at least two first drive members coupled to a first side of the body along the longitudinal axis of the surgical port assembly, and at least two second drive members coupled to a second side of the body along the longitudinal axis of the surgical port assembly, the at least two first drive members and the at least two second drive members forming a set of drive members, the set of drive members configured to operate in coordination to change the position of the distal portion of the surgical instrument.

7. The surgical port assembly of claim 6, further comprising a second set of drive members configured to operate in coordination to change the position of the distal portion of the surgical instrument in a direction different from the direction in which the first set of drive members changes the position of the distal portion of the surgical instrument.

8. The surgical port assembly of claim 1, further comprising a holding member coupled to the body, the holding member configured to maintain a portion of the surgical instrument in a fixed position with respect to the body, the holding member allowing the distal portion of the surgical instrument to move in all directions.

9. A surgical port system including the surgical port assembly of claim 1, the surgical port system further including a surgical instrument, wherein the surgical instrument includes an endoscopic camera.

10. The surgical port system of claim 9, wherein the control interface of the surgical port assembly further includes at least one driver coupled to at least a first one of the plurality of drive members.

11. The surgical port system of claim 10, wherein the first one of the plurality of drive members includes a roller member, and wherein the at least one driver includes a rotary motor mechanically coupled to the roller member, the roller member configured to interface with the surgical instrument and to translate the endoscopic camera along a longitudinal axis of the surgical instrument.

12. A method of controlling a surgical instrument using a surgical port assembly, the method comprising: sensing a position of a distal portion of the surgical instrument relative to a body of the surgical port assembly, the body defining a longitudinal axis; determining whether a button disposed on the surgical instrument is activated; linearly actuating an engagement member of at least one drive member supported by the body of the surgical port assembly; and positioning the engagement member at an acute angle relative to the longitudinal axis of the body to selectively tilt the surgical instrument away from the longitudinal axis of the body to move the distal portion of the surgical instrument to a position that is aligned with a sensed position of the distal portion of the surgical instrument when it is determined that the button is activated.

13. The method of claim 12, wherein sensing the position of the distal portion of the surgical instrument includes sensing a signal transmitted from a transmitter disposed on the distal portion of the surgical instrument.

14. The method of claim 13, further comprising moving the distal portion of the surgical instrument to another position based on the signal transmitted from the transmitter.

* * * * *